United States Patent [19]
Montebello et al.

[11] Patent Number: 5,810,707
[45] Date of Patent: Sep. 22, 1998

[54] DYNAMIC TABLE/SHIELD APPARATUS AND METHOD OF USING SAME IN MOVING-TABLE TOTAL BODY IRRADATION TREATMENT

[75] Inventors: Joseph F. Montebello; Lech S. Papiez, both of Indianapolis, Ind.

[73] Assignee: Advanced Research & Technology Instiute, Indianapolis, Ind.

[21] Appl. No.: 845,472

[22] Filed: Apr. 25, 1997

[51] Int. Cl.$^6$ ..................................................... A61N 5/00
[52] U.S. Cl. .................................................................. 600/1
[58] Field of Search ............................................. 600/1–8

[56] References Cited

PUBLICATIONS

Connors S., Scrimger, J., Logus, W., Johnson, L., Schartner, E.: Development of a translating bed for total body irradiation, Medical Dosimetry 13:195–199, 1988.
Umek, B., Zwitter, M., Habic, H.: Total body irradiation with translation method, Radiotherapy and Oncology 38:253–255, 1996.
Quast, U.: Physical treatment plannin of total body irradiation: Patient translation and beam–zone method, Medical Physics 12(5):567–574, 1985.
Quast, U.: Total body irradiation –review of treatment of treatment techniques in Europe, Radiotherapy and Oncology 9:91–106, 1987.

*Primary Examiner*—John P. Lacyk
*Attorney, Agent, or Firm*—Depaoli & Frenkel, P.C.

[57] ABSTRACT

A dynamic table/shield apparatus contains a movable treatment table and at least one shielding block which is movable relative to the table. The apparatus effects total body irradiation treatment of a body disposed on the table while completely shielding, throughout the treatment time, a midplane of a predetermined body part from a radiation beam emitted from a radiation source during the treatment. During the treatment, the table and body are moved in a first direction at a first velocity $V_1$ through a radiation field, and the shielding block is moved relative to the table at a second velocity $V_2$ in a second direction opposite of the first direction. The second velocity is equal to $(V_1)(b/a)$, wherein "$V_1$" is the first velocity, "b" is the perpendicular distance between the the shielding block and the midplane of the body part, and "a" is the perpendicular distance between the midplane of the body part and the radiation source. The apparatus preferably further contains a movable verification film component for confirming the accuracy of the shielding of the predetermined body part.

15 Claims, 7 Drawing Sheets

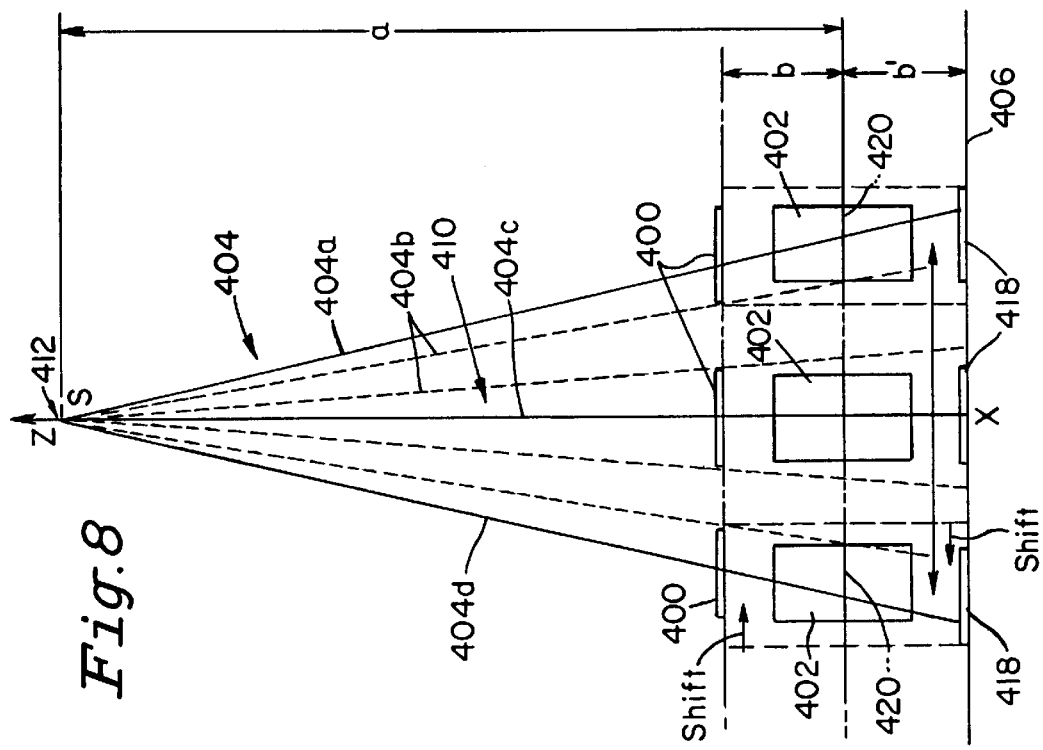
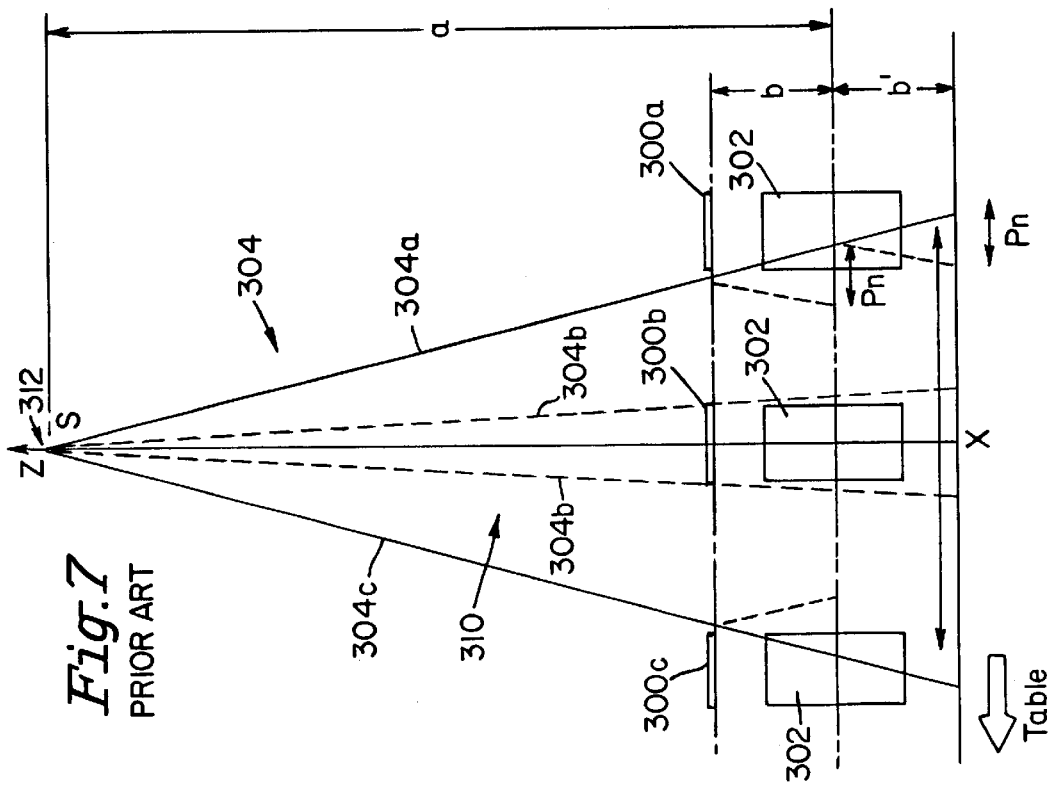

DYNAMIC TABLE/SHIELD APPARATUS AND METHOD OF USING SAME IN MOVING-TABLE TOTAL BODY IRRADATION TREATMENT

BACKGROUND OF THE INVENTION

This invention relates to an apparatus for use in total body irradiation therapy. More particularly, this invention relates to a dynamic table/shield apparatus for use in moving-table total body irradiation therapy. Furthermore, this invention relates to a moving-table total body irradiation method using such apparatus.

In standard radiation therapy, radiation dosage is typically prescribed to a particular part of the body. However, such localized radiation treatment is not always suitable, particularly for a disorder such as acute leukemia wherein leukemic stem cells are distributed throughout the body. Such a disorder requires radiation of the whole body.

Total body irradiation (TBI) is a process whereby the whole body is subjected to radiation therapy. TBI is currently used in conjunction with chemotherapy as a precursor to bone marrow transplants in the treatment of acute leukemia, aplastic anemia, non-Hodgkin's lymphoma, and other hemopoietic and immune deficiency disorders. For example, in the treatment of acute leukemia, intensive chemotherapy is used to sterilize the proliferating leukemic cells and TBI is used to eradicate the remaining stem cells. Furthermore, in allogenic bone marrow transplants, TBI is used to suppress immune reactions to the transplanted tissue.

One technique for effecting TBI treatment involves placing a patient on a treatment table and exposing the patient to a beam of radiation, wherein neither the treatment table nor the radiation beam is moved during the TBI treatment. This technique, referred to herein as "stationary-table TBI treatment", has several drawbacks.

The drawbacks of stationary-table total body irradiation treatment are mainly due to the fact that TBI is not a typical therapy for which radiation oncology facilities are specifically designed. For example, because standard radiation therapy, as mentioned previously herein, usually involves prescribing radiation doses to a particular part of the body rather than to the entire body, most teletherapy units (which are equipped with a radiation source and a treatment table) are designed to treat localized volumes (i.e., parts of the body, rather than the entire body). The maximum radiation field provided by most teletherapy units is generally not greater than 40×40 square centimeters. The field coverage for such units may be increased by increasing the distance between the source and the patient. However, the available treatment distances between the source and the treatment table which is part of the teletherapy unit are rarely large enough to encompass the wholly stretched patient body.

To overcome the problem of insufficient treatment distances between the source and the teletherapy unit's treatment table, treatment tables have been used which are separate and apart from the teletherapy unit's table. The treatment is spaced from the radiation source by a distance needed to effect TBI. A patient is placed on the separate treatment table, either on his/her side or on his/her front or back. The radiation source is rotated or otherwise manipulated so as to direct radiation toward the patient disposed on the separate table.

In some cases, the patient lies on the separate table on his/her back or front side so that the radiation passes through the patient's side. Because the patient's arms are relatively dense, the arms act as a shield to protect the patient's lungs from the radiation. However, with this radiation technique, dose homogeneity tends to suffer.

Frequently, the patient is placed on the separate table on his/her side so that the front or back of the patient faces the radiation source. A shield is disposed on or in front of the lungs to protect them from radiation. However, this approach has several drawbacks. The positioning and maintaining of the shield in the appropriate location tends to be difficult and awkward, making it relatively difficult to accurately shield the lungs or other body part to be shielded. Furthermore, for a patient suffering from cancer or other serious affliction, particularly if the patient is a child, lying on his/her side is relatively uncomfortable, particularly for the period of time required for treatment. Thus, in this second approach, shielding accuracy and patient comfort suffer.

A further disadvantage associated with placing a patient on a separate table and positioning the patient, table and shield for total body irradiation is that this approach is relatively difficult and time-consuming to setup.

In another technique which has been used to overcome the problem of insufficient treatment distances between the source and the teletherapy unit's treatment table, a patient is made to stand at a distance from the radiation source. A shield is placed in front of the patient at the appropriate location. This approach is even more uncomfortable for the patient, particularly since the patient is not supposed to move during the radiation treatment.

In stationary-table TBI treatments, the inconvenience of patient positioning, combined with the duration of a single TBI treatment, compromises both the accuracy of the shielding of sensitive organs and the reproducibility of setups for fractionated treatments.

A second type of TBI technique, known as "moving-table total body irradiation treatment", overcomes many of the problems associated with the stationary-table TBI technique. For example, in moving-table TBI therapy, the table (and patient disposed thereon) moves horizontally through a vertical radiation beam, thus allowing the patient to lie in the more comfortable supine or prone position during treatment. Furthermore, moving-table TBI treatment has been found to provide superior dose homogeneity as compared to stationary-table TBI treatment.

Moving-table TBI therapy is discussed, e.g., in the following articles: Connors, S., Scrimger, J., Logus, W., Johnson, L., Schartner, E.: *Development of a translating bed for total body irradiation*, Medical Dosimetry 13:195–199, 1988; Umek, B., Zwitter, M., Habic, H.: *Total body irradiation with translation method*, Radiotherapy and Oncology 38:253–255, 1996; Quast, U.: *Physical treatment planning of total body irradiation: Patient translation and beam-zone method*, Medical Physics 12(5):567–574, 1985; and Quast, U.: *Total body irradiation—review of treatment techniques in Europe*, Radiotherapy and Oncology 9:91–106, 1987. Each of the foregoing articles is hereby incorporated by reference herein.

Although moving-table TBI treatment has overcome many of the problems associated with stationary-table TBI treatment, moving-table TBI faces the challenge of providing precise shielding of radiation-sensitive body parts during the table's motion through the beam.

TBI processes typically involve the application of relatively high doses of radiation to the body. These relatively high levels of radiation may reach or exceed the radiation-tolerance of certain vital organs, e.g., the lungs, and can lead to radiation pneumonitis.

Thus, the challenge of TBI treatment is to deliver the radiation dose as homogeneously and as precisely as possible to provide uniform killing of the cells to be eradicated, e.g., leukemic stem cells, but without overdosing vital organs.

To achieve this goal, shielding has been used to protect sensitive organs from radiation during TBI treatment.

One method for shielding a sensitive organ from radiation during a moving-table TBI treatment involves mounting an attenuating block above a patient and keeping the block moving with the table during treatment so that the table and block do not change positions relative to one another during table motion. In other words, in the table system of coordinates, the block and the table do not move relative to one another. However, such technique, referred to herein as "stationary-block TBI treatment", has been found to result in imprecise shielding of the sensitive organ. Because the radiation beam is divergent, radiation is able to enter the shielded organ at the front end of the shielding block when the shielded organ enters the field of radiation. Similarly, when the shielded organ leaves such radiation field, radiation is blocked from the tissue extending forward from the shielded organ. These effects are responsible for dose smearing at the edge of the shielded organ during the moving-table TBI process.

Accordingly, a primary object of this invention is to provide a table/shield apparatus for use in moving-table TBI processes, wherein the table/shield apparatus provides more precise shielding of sensitive organs during the TBI process.

A further object of this invention is to provide a table/shield apparatus for use in moving-table TBI processes, wherein the apparatus provides homogeneous irradiation of the whole body while precisely shielding sensitive organs.

A further object of this invention is to provide a table/shield apparatus which contains a verification means for verifying the accuracy of shielding achieved with the apparatus.

Another object is to provide a moving-table TBI method which uses a table/shield apparatus having the above-mentioned characteristics.

These and other objects which are achieved according to the present invention can be discerned from the following description.

SUMMARY OF THE INVENTION

The present invention is based on the discovery that precise shielding of sensitive organs during moving-table TBI therapy can be achieved when the shielding block is moving relative to the patient (in the table system of coordinates) during the movement of the table through the radiation beam. The present invention is further based on the discovery that undistorted image verification of such shielding can be achieved if a verification film disposed under the top portion of the table (i.e., under the patient) is also moving relative to the table during the motion of the table through the beam.

One aspect of the present invention is directed to a dynamic table/shield apparatus for effecting total body irradiation treatment of a body while shielding a midplane of a predetermined part of the body from a radiation beam emitted from a radiation source used in the treatment. Such apparatus contains:

(A) a movable treatment table capable of movement in a first direction at a first velocity, the table containing a top portion for repose thereon of the body; and (B) at least one movable radiation-shielding block for shielding the midplane of the predetermined body part, the block being capable of movement relative to the table in a second direction opposite to the first direction and at a second velocity in the table system of coordinates, the second velocity being calculated according to the formula $V_2=(V_1)(b/a)$, wherein "$V_2$" is the second velocity, "$V_1$" is the first velocity, "b" is the perpendicular distance between the shielding block and the midplane of the predetermined body part, and "a" is the perpendicular distance between the radiation source and the midplane of the predetermined body part.

Preferably, the apparatus of this invention further contains (C) a movable radiation-sensitive verification film component disposed under the top portion of the table, wherein the verification film component is capable of movement relative to the table at a third velocity in the first direction. The third velocity is calculated according to the formula $V_3=(V_1)(b'/a)$ wherein "$V_3$" is the third velocity, "$V_1$" is the first velocity, "b'" is the perpendicular distance between the verification film component and the midplane of the predetermined body part, and "a" is the perpendicular distance between the radiation source and the midplane of the predetermined body part.

A second aspect of this invention is directed to a method of effecting total body irradiation treatment of a body while shielding a midplane of a predetermined part of the body from a radiation beam emitted from a radiation source used in the treatment. The method involves:

(1) providing the dynamic table/shield apparatus of this invention;

(2) providing the radiation source and causing the radiation source to emit the radiation beam toward a plane of the table such that a central axis of the beam is perpendicular to the plane, the beam forming a radiation field on the plane;

(3) placing the body on the treatment table such that a front end of the midplane of the predetermined body part is disposed toward the radiation field and an opposite back end of the midplane of the body part is disposed away from the radiation field;

(4) causing the table to move at the first velocity in the first direction through the radiation field such that the front end of the midplane of the body part enters the radiation field before the back end of the midplane of the predetermined body part;

(5) before or during step (4), aligning the shielding block and the midplane of the predetermined body part such that when the midplane is disposed in a beam-entry position, the shielding block is disposed in an initial block position; wherein in the beam-entry position, the midplane is disposed such that a first diverging edge of the beam is aligned so as to contact a front end of the midplane; further wherein in the initial block position, the shielding block is disposed such that a front end of the block is in contact with the first diverging edge of the beam so as to shield the midplane from the first diverging edge; and (6) when the shielding block is disposed in the initial block position and the midplane is disposed in the beam-entry position, causing the shielding block to move at the second velocity in the second direction opposite to the first direction in the table system of coordinates; whereby during movement of the table through the radiation field, the midplane of the predetermined body part is continuously and completely shielded from the radiation beam by the shielding block.

The dynamic table/shield apparatus and method of this invention provide a number of benefits. Specifically, the apparatus and method of this invention provide superior dose distribution uniformity throughout the patient's body; provide precise shielding of sensitive organs during the TBI therapy; allow accurate verification of such shielding of sensitive organs; allow the patient to be disposed in a relatively comfortable supine or prone position on the top portion of the table during the TBI therapy; are relatively economical; and allow relatively easy standardization of setups, calculations and verifications and, thus, can be easily implemented.

BRIEF DESCRIPTION OF THE DRAWINGS

FIG. 7 is a schematic side view of a prior art table/shield apparatus during fixed moments of a prior art moving-table total body irradiation process.

FIG. 8 is a schematic side view of a dynamic table/shield apparatus within the scope of the present invention during fixed moments of the moving-table total body irradiation method of this invention, wherein the apparatus further contains a verification film disposed on a movable tray.

DETAILED DESCRIPTION OF THE INVENTION

As stated above, one aspect of the present invention is directed to a dynamic table/shield apparatus for use in moving-table total body irradiation therapy.

As used herein, the term "dynamic table/shield apparatus" refers to a table/shield apparatus wherein the shielding block(s) moves relative to the table during the movement of the table.

As used herein, the terms "relative to the table" and "table system of coordinates" both refer to the system of coordinates wherein the table is the reference point for determining motion of other objects. For example, in the stationary-block technique mentioned previously herein, the shielding block and the table move at the same velocity. Thus, to one sitting on the table and observing the shielding block, the shielding block would not appear to be moving because the table is moving at the same speed as the block. Thus, in such case, the block is "stationary" or "motionless" relative to the table. In the present invention, the shielding block is moving at a different velocity than is the table. Thus, to one sitting on the table and observing the shielding block in the present invention, the block would appear to be moving because the block and table are moving at different speeds. Thus, in the present invention, the block is "dynamic" or "movable" relative to the table.

As used herein, the term "room system of coordinates" refers to a system wherein the room is the reference point for detecting motion. For example, in the stationary-block situation discussed above, a person located in a room with the table and shielding block but not disposed on either the table or block, would observe that the block and table are both moving (at the same speed). In the moving-block situation of the present invention, such a person located in the room would also observe that the table and block are both moving (at different velocities).

The apparatus of this invention contains a movable treatment table, at least one movable shielding-block, and, preferably, a movable verification film component which verifies the shielding accuracy of the shielding-block(s). The table has a top portion on which the patient rests during the TBI procedure. The shielding-block(s) is preferably disposed on a movable block-supporting tray which is adjustable in height relative to the table. If present, the film component is preferably disposed on a movable film-supporting tray located underneath the top portion of the table.

The dynamic table/shield apparatus of this invention will be described by reference to FIGS. 1–4 herein.

Figure 1:
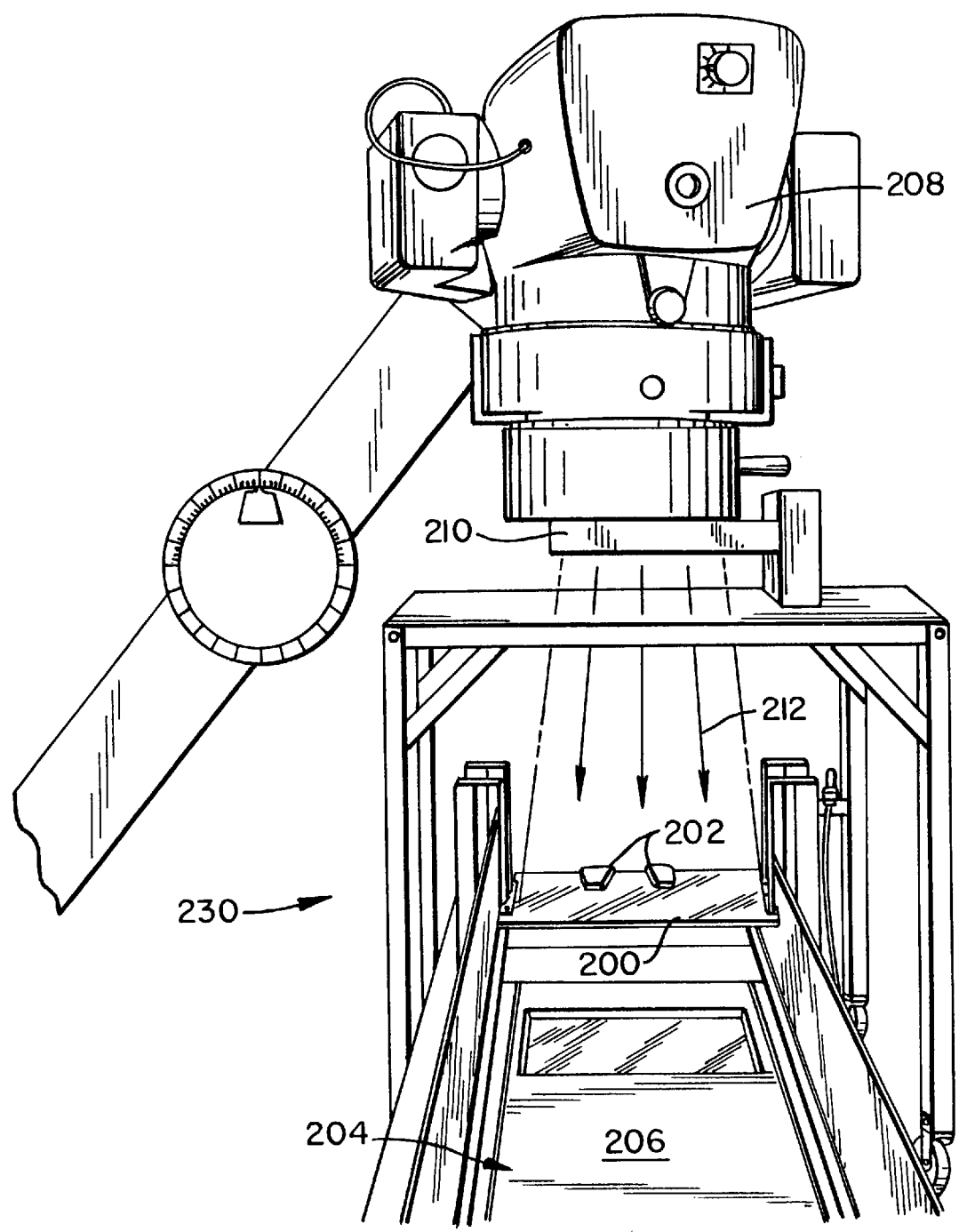
FIG. 1 is a perspective view of one end of a dynamic table/shield apparatus within the scope of the invention and a Cobalt unit.
Figure 2:
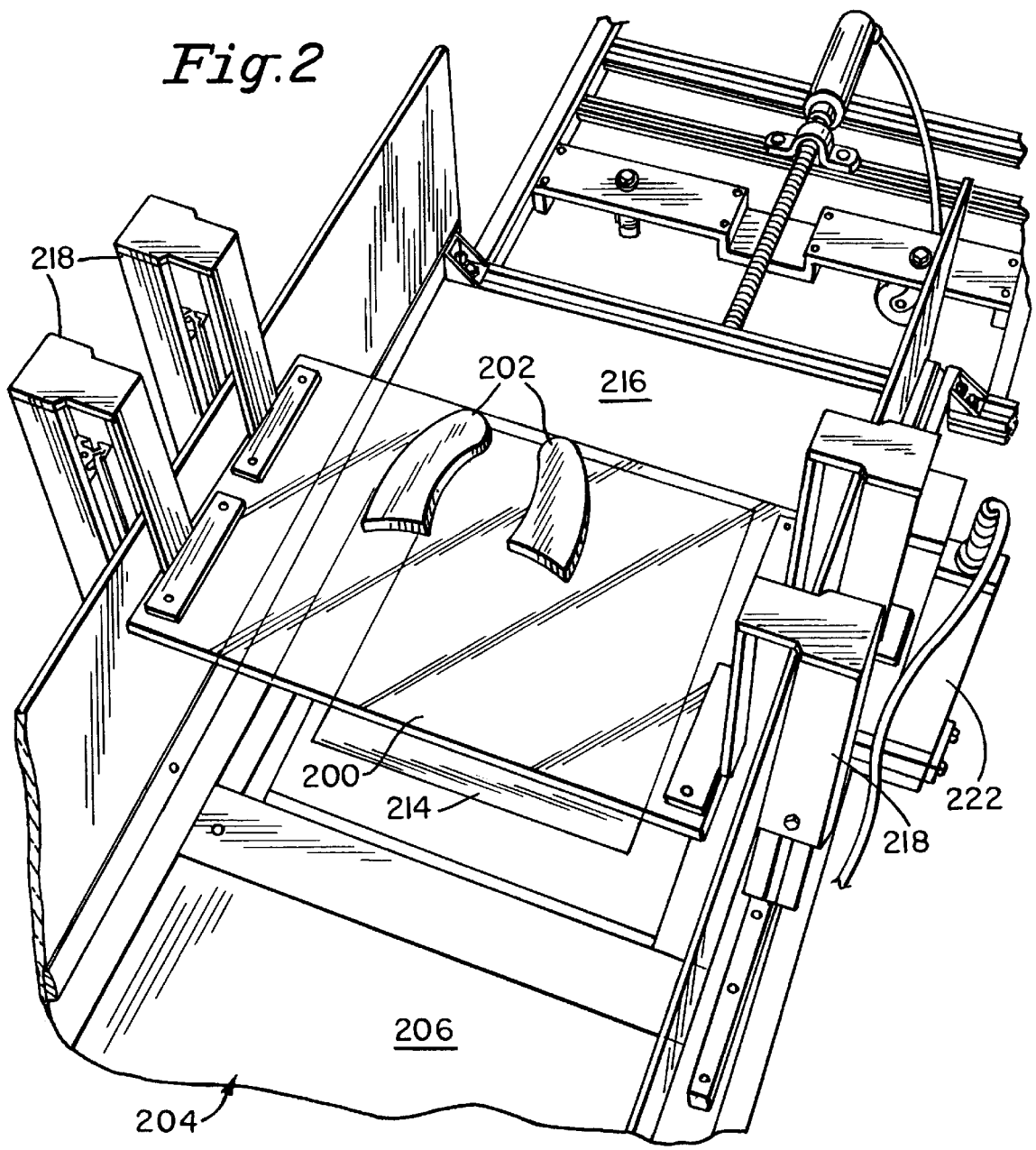
FIG. 2 is a perspective top view of the apparatus shown in FIG. 1.
Figure 3:
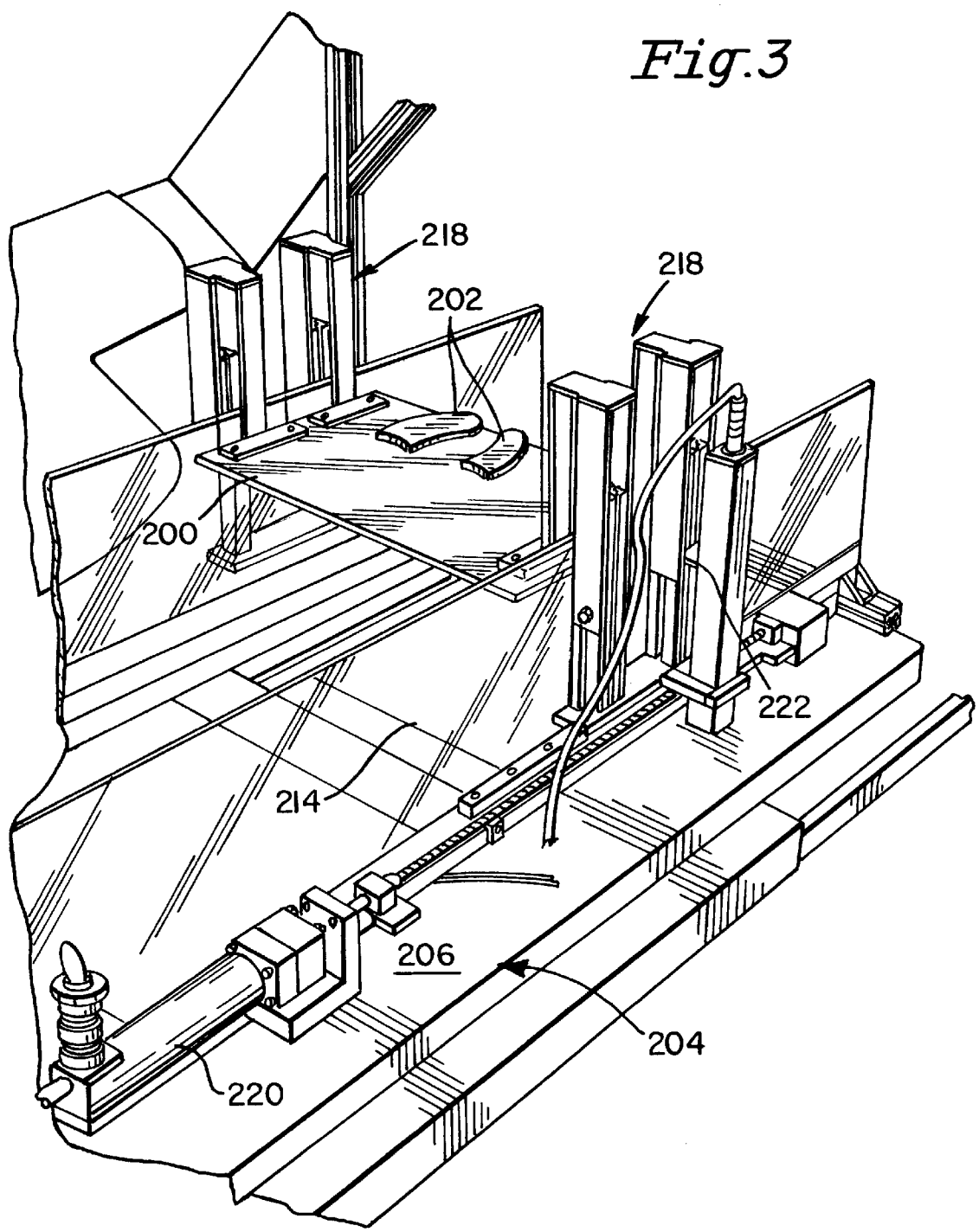
FIG. 3 is a perspective side view of the apparatus shown in FIG. 1.
Figure 4:
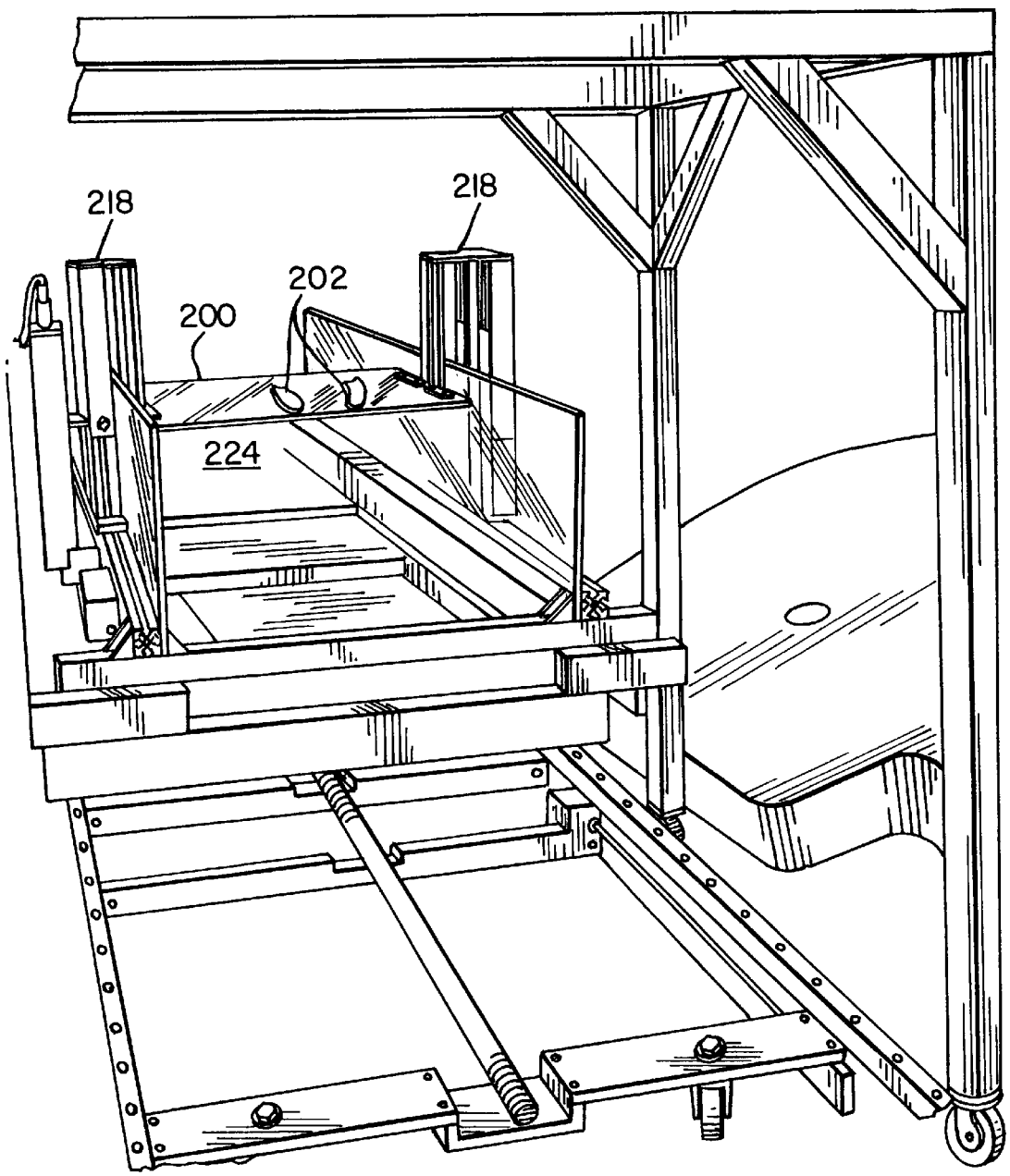
FIG. 4 is a perspective view of an opposite end of the apparatus shown in FIG. 1.

In FIGS. 1–4, a dynamic table/shield apparatus 230 is composed of a movable treatment table 204 and two shielding-blocks 202 disposed on a block-supporting tray 200. Table 204 has a top planar portion 206 on which a patient (not shown) lies during the TBI treatment. Top portion 206 has a head-receiving part 216 on which the patient's head rests during the treatment (FIG. 2) and a feet-receiving part 224 on which the patient's feet are disposed during treatment (FIG. 4).

Blocks 202 and block-supporting tray 200 are situated between top portion 206 of table 204 and a radiation source 208 (e.g., a Cobalt 60 unit), which may contain a beam attenuator 210. In FIGS. 1–4, block-supporting tray 200 is shown attached to table 204 by a plurality of height-adjustable tray supports 218. Tray supports 218 are height-adjustable so that the distance between the block-supporting tray 200 and the patient, as well as the distance between tray 200 and the radiation source 208, can be adjusted as needed. In preferred embodiments, apparatus 230 further contains a height sensor 222 which is capable of sensing the position of the shielding blocks 202 and tray 200 relative to the table.

In apparatus 230, blocks 202 are disposed to shield the lungs (not shown) of the patient (one shielding-block per lung) from beam 212 emitted by radiation source 208.

Apparatus 230 preferably further contains a verification film component 214 disposed on a film tray (not shown) underneath top portion 206 of table 204.

Preferably, apparatus 230 contains a first motor 220 (FIG. 3) which causes shielding blocks 202, blocking-tray 200 and tray supports 218 to move in the desired direction and at the desired velocity discussed later herein.

Also preferably, apparatus 230 contains a second motor (not shown) which causes treatment table 204 (and the patient disposed thereon during the TBI treatment) to move in the desired direction and at the desired velocity discussed later herein.

If apparatus 230 further contains a verification film component, the apparatus will preferably contain a gear mechanism (not shown) connected to the film component to cause the movement of the film component in the desired direction and at the desired velocity discussed herein.

The shielding block(s) used in the apparatus and method of this invention is preferably composed of a fusible metal alloy having a melting point which is lower than the boiling point of water (i.e., lower than about 100° C.). Preferably, such fusible metal alloy contains lead, bismuth, cadmium and tin. A particularly suitable fusible metal alloy containing lead, bismuth, cadmium and tin is available from Cerro Corporation under the designation "Cerrobend".

The shape of the shielding block(s) is determined using localization film at the table position routinely used as a reference, where the body part to be shielded (e.g., the lungs) is approximately centered in the non-moving field. The block is drawn on the film in the conventional manner and a straight edge block is cut from the film.

The thickness of the shielding block(s) is that thickness which provides the desired amount of radiation attenuation. Preferably, the shielding block(s) has a thickness of from about 1 to about 6 centimeters.

A second aspect of this invention is directed to a method of effecting moving-table total body irradiation using the dynamic table/shield apparatus of this invention.

In the present invention, accurate shielding, as well as its undistorted image verification, is achieved when the shielding block(s) and verification film component are moving relative to the patient (table) in the table system of coordinates during the table motion under the beam. The motion of the blocks and film tray and the motion of the patient (table) are to be coordinated so that the midplane of the shielded body part, as well as the image of the shielding block and shielded body part at the film level, are permanently kept in the shielding block's shadow relative to the radiation rays emanating from the radiation source.

Specifically, in the method of this invention, the shielding block is moved through the radiation field at a second velocity $V_2$ in the table system of coordinates, the second velocity being calculated by the formula: $V_2=(V_1)(b/a)$, wherein "$V_2$" is the second velocity, "$V_1$" is the first velocity, "b" is the perpendicular distance between the shielding block and the midplane of the predetermined body part, and "a" is the perpendicular distance between the radiation source and the midplane of the predetermined body part.

If the apparatus of this invention further contains a verification film component, such component is moved at a third velocity $V_3$ in the table system of coordinates, such third velocity being calculated according to the formula: $V_3=(V_1)(b'/a)$ wherein "$V_3$" is the third velocity, "$V_1$" is the first velocity, "b'" is the perpendicular distance between the verification film component and the midplane of the predetermined body part, and "a" is the perpendicular distance between the radiation source and the midplane of the predetermined body part.

The velocity of the table depends on several factors, including the size of the patient. The velocity of the table must be such that the patient receives the correct amount of dose. Typically, the velocity of the table will range from about 55 millimeters to about 75 millimeters per minute.

The movement of the table, shielding block and verification film component is preferably in a horizontal direction relative to the central axis of the radiation beam. In addition, the table, shielding block and verification film component preferably move through the beam in linear fashion.

The method of this invention will be described with reference to FIGS. 5, 6 and 8 herein.

Figure 5:
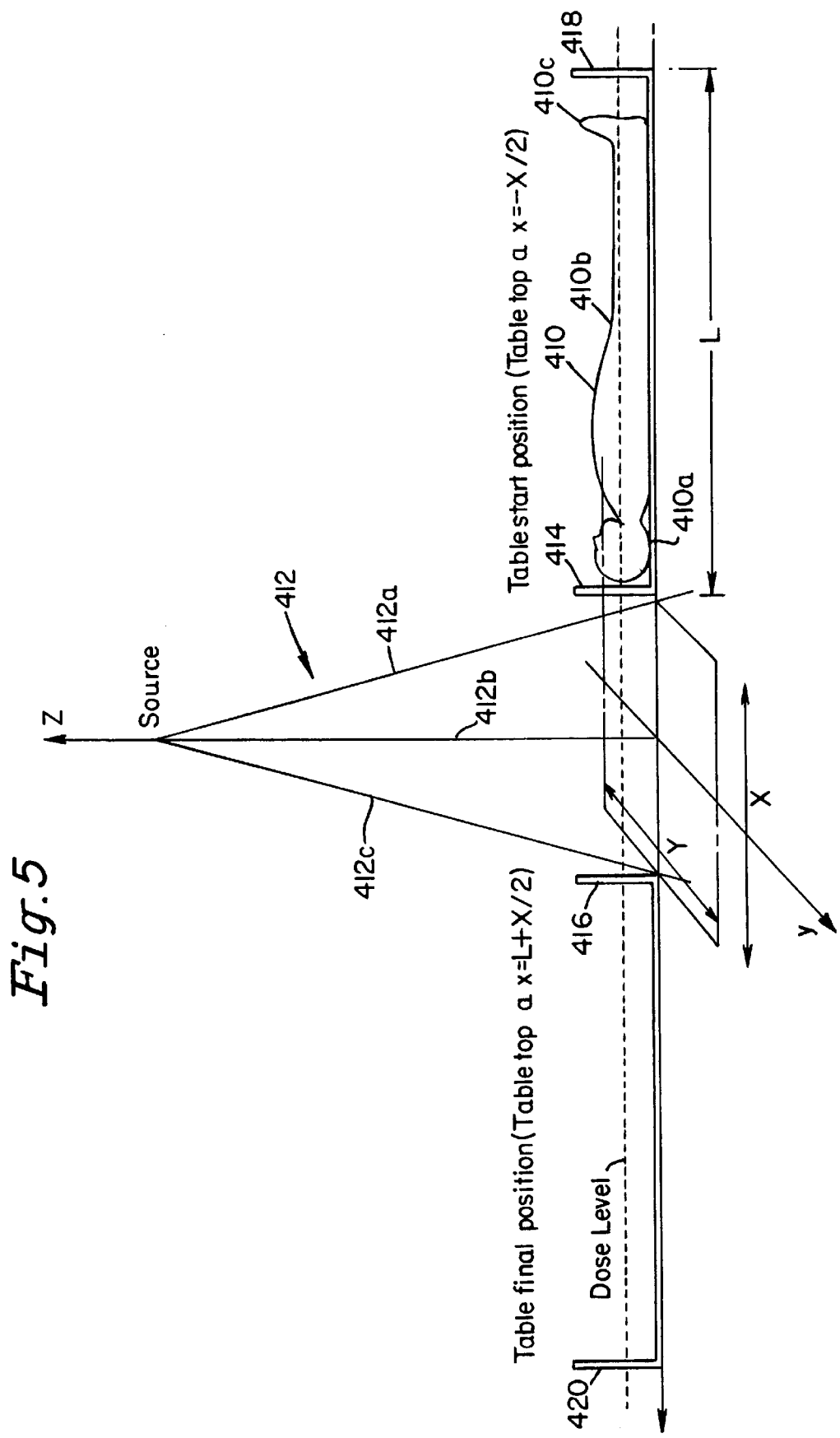
FIG. 5 is a schematic side view of a dynamic table/shield apparatus within the scope of the present invention during fixed moments of the moving-table total body irradiation method of this invention.

In FIG. 5, a radiation source S is provided which emits a divergent radiation beam 412 which forms a radiation field R at the plane of table 414. Radiation field R has a length X along the x axis and a width Y along the y axis. The y axis is perpendicular to the x axis. Radiation beam 412 has a height 412b along the z axis, the z axis being the central axis of beam 412. The z axis is perpendicular to the x axis and to the y axis and, thus, is perpendicular to the plane of table 414 and the direction of table motion. Radiation beam 412 further has a first diverging edge 412a and a second diverging edge 412c.

Table 414 has a front end 414a, an opposite back end 414b, and a length L which extends along the x axis between front end 414a and back end 414b.

In FIG. 5, linear motion of table 414 will proceed along the x axis.

A patient 410 is disposed in supine or prone position on table 414. The head 410a of patient 410 is disposed in proximity to front end 414a of table 414, and the feet 410b of patient 410 are disposed in proximity to the back end 414b of table 414. Thus, head 410a of patient 410 enters radiation field R before feet 410b do.

The midplane of the lung (not shown) of patient 410 is disposed along axis m (shown in dashed lines) in FIG. 5.

At the beginning of the TBI method of this invention, patient 410 will lie completely outside of the radiation field R.

As shown in FIG. 5, during the TBI method of this invention, treatment table 414 travels from initial table position T1, through the length X of radiation field R, to final table position T2. As used herein, the terms initial table position T1 and final table position T2 refer to the respective positions of the front end 414a of table 414 at the beginning and end of the TBI procedure. Preferably, at both initial table position T1 and final table position T2, table 414 is situated completely outside of radiation beam 412 (i.e., both the forward end and the back end of the table are outside the beam). Initial table position T1 is located on axis x on one side of central point C and final table position T2 is located on axis x on the opposite side of central point C. In other words, central point C is situated between the initial and final table positions. The distance between central point C and initial table position T1 is preferably about X"/2 (X" being the length of radiation field R"). The distance between central point C and final table position T2 is preferably about (L"+X"/2), wherein L" represents the length of table 414.

Figure 6A:
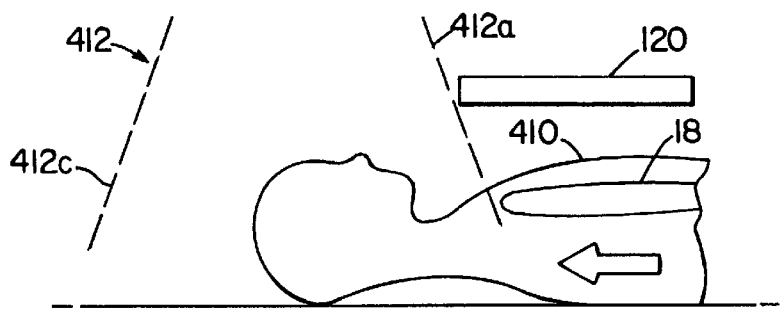
FIGS. 6a–6c represent schematic views of a series of fixed moments during the moving-table total body irradiation method illustrated in FIG. 5.
Figure 6B:
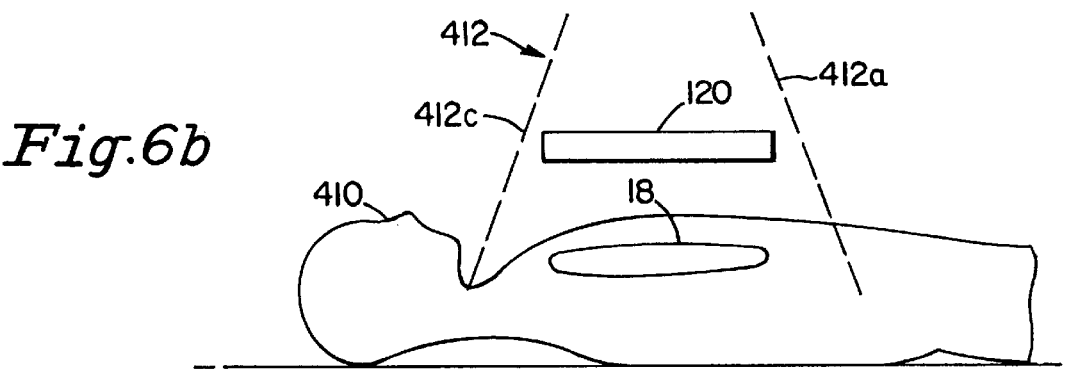
Figure 6C:
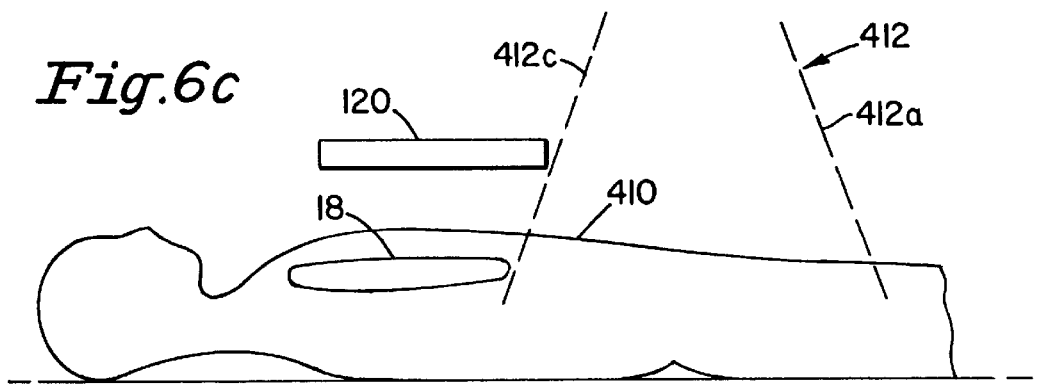

FIGS. 6a–6c illustrate fixed moments of a moving-table TBI method within the scope of the present invention.

Initially, patient 410 lies to the right of radiation field R formed by radiation beam 412. As the treatment begins, patient 410 is slowly moved to the left such that the head 410a of body 410 enters the first diverging edge 412a of beam 412. At this point, shielding block 120 is positioned outside of radiation field R, thereby providing no attenuation to the beam 412.

The shielding block 120 remains outside of radiation field R until the moment illustrated in FIG. 6a, wherein first diverging edge 412a of beam 412 begins to contact the leftward (i.e., front) end 18a of the midplane of lung 18. This position of the midplane is referred to herein as "the beam entry position". At or prior to this moment, shielding block 120 is moved to the position shown in FIG. 6a, wherein a front end 120a of block 120 is disposed in contact with the first diverging edge 412a of beam 412. This position of the shielding block is referred to herein as the "initial block position". When the midplane is in the beam-entry position, the block is disposed in the initial block position. The table is then moved through the radiation field at the first velocity and the shielding block is moved at the second velocity.

Thus, leftward movement of patient 410 through radiation field R is accompanied by leftward movement (in the room system of coordinates) of shielding block 120 such that block 120 is always in the correct position to completely shield the midplane of lung 18 from radiation beam 412.

As shown in FIG. 6b, when the lung 18 is positioned substantially in the center of radiation field R, the shielding block 120 is preferably positioned substantially above lung 18. In order to move block 120 from the position shown in FIG. 6a to the position shown in FIG. 6b, the block 120 needs to move in the leftward direction at a slower speed (in the room system of coordinates) than does patient 410.

The relative disparity between the speed of block 120 and the speed of patient 410 continues until the back (right) end 18b of lung 18 leaves second diverging edge 412c of beam 412 (FIG. 6c). At this point, the back end 120b of block 120 is also just leaving second diverging edge 412c of beam 412. Once lung 18 has exited radiation field R, the relative motion of block 120 with respect to patient 410 is not critical. It is only important that block 120 not reenter beam 412 as this would provide attenuation to beam 412 when such is not desired. In a preferred embodiment, block 120 continues its leftward movement at the same rate as the table throughout the remaining part of the TBI procedure once the lung 18 has exited radiation field R.

The velocity of the block through radiation field R respective to the room system of coordinates is lower than the velocity of the patient (table) through radiation field R. The block moves at a lower velocity than does the patient in order to account for the fact that the rays of the beam strike the patient at increasingly sharper incident angles until the rays become perpendicular to the patient in the center of radiation field R. As a result of the lower velocity of the block relative to the velocity of the patient, a given point in the shielded body part and a given point in the block always lay along a ray of the beam (i.e., a straight line connecting these two points always passes through the radiation source).

The following items of information, which may be determined with some precision prior to the start of the TBI procedure, can be used to calculate the required motion and speed of the block with respect to the table:

the speed of the table required to deliver the correct dose under the condition of a given (fixed) dose rate;

the position of the head and feet of the patient;

the position of the lungs (or other shielded body part) within the patient;

the location of the first diverging edge and the second diverging edge of the radiation beam, as well as their incident angles; and the distance between the radiation source and the top surface of the table, as well as the distance between the shielding block and the patient.

FIG. 7 illustrates the challenge of providing accurate shielding of sensitive organs (e.g., lungs) during a stationary-block TBI treatment, wherein the shielding block does not move relative to the table in the table system of coordinates during the TBI procedure.

In FIG. 7, a shielding block 300 is mounted above a lung 302 of a patient (not shown) and is moved with the table (not shown) during TBI treatment in the direction indicated so that in the table system of coordinates, block 300 and the table (and patient) are motionless relative to one another. As can be seen in FIG. 7, the lack of motion of the block 300 relative to the table in the table system of coordinates leads to imprecise shielding of lung 302. The divergence of radiation beam 304 emitted by radiation source S is responsible for the penetration of diverging beam edge 304a inside the shielded lung 302 on the front edge 300a of block 300 at the time the lung 302 enters the radiation field R formed by beam 304 at the level of the table (see block position B1 in FIG. 7). When the lung 302 is positioned substantially in the center of radiation field R as indicated by dashed lines 304b, the shielding block 300 is positioned substantially above lung 302 (see block position B2 in FIG. 7). Similarly, when shielded lung 302 is leaving radiation field R, diverging beam edge 304c is being blocked from tissue (not shown) extending forward from shielded lung 302 (see block position B3 in FIG. 7). These effects are responsible for dose smearing at the edge of shielded lung 302.

FIG. 8 illustrates the shift of a shielding-block tray 400 and the shift of a verification film tray 406 during the movement of the table in the moving-table TBI process of this invention.

In FIG. 8, the verification film tray 406 is disposed under the patient (not shown). Shielding-block tray 400 is mounted above a lung 402 of the patient disposed on a movable treatment table (not shown). During moving-table TBI therapy, shielding-block tray 400 is moved relative to the patient during the motion of the table through radiation field R formed at the level of the table by a radiation beam 404 emitted from a radiation source S. Beam 404 has a height 404c at central axis z. The motion of shielding-block tray 400 relative to the table and the patient is to be coordinated so that the midplane m of shielded lung 402, as well as the image (not shown) of shielded lung 402 and shielding-block tray 400 on the film 406, is permanently kept in the shadow of tray 400 relative to beam 404. Based on the table system of coordinates, film tray 406 moves in the same direction as the table, and block tray 400 moves in the opposite direction. Based on the room system of coordinates, film tray 406 and block tray 400 move in the same direction as the table.

In the table system of coordinates, the shift of block tray 400 assures the precise shielding of the midplane of the sensitive organ and the shift of film tray 406 assures the accurate image of the shielding of the sensitive organ on the film.

Block tray 400 travels through length X of radiation field R at a velocity $V_2$ calculated according to the following formula:

$$V_2 = (V_1)(b/a)$$

wherein "$V_2$" is the velocity of the block in the table system of coordinates, "$V_1$" is the velocity of the table, "b" is the distance between the shielding block and the midplane of the body part to be shielded, and "a" is the distance between the radiation source and the midplane of the body part to be shielded (see FIG. 8).

The velocity of verification film tray 406 relative to the table can be calculated according to the following formula:

$$V_3 = (V_1)(b'/a)$$

wherein "$V_3$" is the velocity of the film tray in the table system of coordinates, "$V_1$" is the velocity of the table, "b'" is the distance between the verification film and a midplane of the predetermined body part, and "a" is the distance between the radiation source and the midplane of the predetermined body part.

Although FIGS. 5, 6 and 8 illustrate the shielding of a lung, it is to be understood that the apparatus and method of this invention may be used to shield other body parts, e.g., the ovaries, gonads, stomach, and the like, which are desired to be shielded.

In the method of this invention, the patient is preferably disposed on the table in a supine or prone position. The supine or prone positioning of the patient on the table allows the patient to be relatively comfortable during the TBI treatment and minimizes body motions during irradiation. The patient is easily immobilized (e.g., in a vac lock bean bag on the table and his/her position relative to the table, shielding block(s) and radiation beam is easily reproducible from one TBI treatment to another. Such reproducibility of the patient's position is helpful to achieving accurate shielding of sensitive organs.

To minimize differences in dose distributions from scattered radiation to various anatomical structures and for different size patients, bolusing (not shown) around the patient during the treatment may be required.

The source of radiation used in the present invention can be any of the conventional radiation sources used in radiation therapy procedures. Preferably, the radiation source used in the present invention is a Cobalt 60 unit or an X-ray therapy accelerator.

In the method of this invention, the radiation source contains collimators (not shown) which control the length X and width Y of radiation field R. During the TBI method of this invention, the collimator which controls length X of radiation field R is preferably opened as fully as possible. Under conditions of fixed dose rate, a maximal length X of the radiation field minimizes patient treatment time. Furthermore, the opening of the collimator which defines the width Y of radiation field R will be as large as necessary to encompass the most broad patient in the field. Maintaining constant X and Y field sizes for all patients and all treatments allows the dose calculations for moving-table TBI to be easily standardized and reduces the chances of calculational or setup errors.

In the method of this invention, the distance between the patient and the radiation source will depend on a number of factors.

The main restriction on the minimal distance between the radiation source and the patient is imposed by the minimal field size in the Y direction (i.e., Field Y). As mentioned hereinabove, the size of the field in the Y direction has to be large enough to encompass the most broad patient. For example, if the maximal field size required in the Y direction is approximately 60 centimeters, then the minimal distance between the source and the midplane of the patient is preferably in the range of from about 130 to about 150 centimeters, depending on the maximum collimator setting at isocenter.

In principle, there are no restrictions for the maximal distance between the patient and the radiation source other than limits imposed by relative positioning of the radiation source in the treatment room, size and the minimum dose rate required for the TBI treatment. A greater distance between the radiation source and the patient has an obvious advantage over a shorter distance because the greater distance will result in increased field coverage in the X direction and thus decreases the time of patient exposure. Such large-distance treatment has the shortcoming of decreased dose rate flexibility. With a maximum dose rate of the Cobalt 60 source being approximately 250 cGy/min at 80 centimeters in free space, the dose rate at 3 meters is approximately 18 cGy/min in free space, and after only one-half life time, the Cobalt source dose rate starts to approach unacceptably low values for larger patients. At shorter distances between the radiation source and the patient, the dose rates are greater and can be reduced for TBI treatments with the use of attenuating filters. By applying variable attenuation of the beam (e.g., with variable number of lead sheets), it is possible to keep dose rates during treatment in the optimal range for extended periods of time. In particular, for moving-table Cobalt 60 therapy administered at a distance of roughly one-half of the stationary therapy, it is possible to maintain dose rates within acceptable limits for 15–20 years, i.e., considerably longer than the lifetime of a radiation source for standard radiation therapy or standard stationary TBI therapy using a Cobalt 60 source disposed at relatively large distances from the patient.

The distance between the shielding block(s) and the top surface of the patient will preferably range from about 5 to about 10 centimeters. As mentioned previously herein, the apparatus of this invention preferably contains a means for adjusting the distance between the shielding block(s) and the patient.

If the apparatus of this invention contains a verification film as discussed above, the distance between the film and the patient is preferably from about 5 to about 10 centimeters.

In addition to providing greater patient comfort and more precise shielding of sensitive organs during TBI, the present invention also provides relatively good dose homogeneity. It is well known that dose rate in free space decreases with inverse square of the distance between the point source of radiation and the point of dose rate measurement. This law of inverse square dependence of dose rate on the distance is a consequence of inverse square decrease in photon fluence with distance between the source and the measurement point. If the dose rate in free space at distance "r" from a point source is denoted by "DR(r)" then the above property can be expressed as $DR(r)=C/r^2$ where "C" is a constant specific for a given source ("C" can be interpreted, for example, as the dose rate at distance 1, i.e., $C=DR(1)$). If, however, in the case of a cumulative dose "$D_c(r)$" absorbed along the full arc of radius "r" and centered at the source, it is found that $D_c(r)=2\|r(C/r^2)=2\|(C/r)$. Similarly, the cumulative dose "$D_{c,a}(r)$" along the arc of angular length "a" at distance "r" from the source (i.e., along the arc of linear length "ar") is given by $D_{c,a}(r)=ar(C/r^2)=a(C/r)$. The same dose will also be accumulated by the linear detector placed at distance "r" from the source that is collimated so that the angular opening of the cone is equal to "a". Thus, the dependence of dose, accumulated in free space by the small mass of tissue that travels on the moving table along a straight line trajectory during TBI therapy, on the distance between the source and the straight line trajectory, is an inverse linear function of the distance rather than an inverse square function. This in turn leads to better effective penetration of tissue by X rays during moving table treatment therapy than during stationary treatment therapy.

The following examples illustrate but do not limit the present invention.

EXPERIMENTAL

In the examples and comparison examples below, a Picker 9 Cobalt 60 unit was used as the radiation source. The distance between the radiation source and the planar top surface of the table was 144 cm. The collimator for the TBI treatments, as well as for all calibrations and measurements, was fully open to define the largest field possible. These field dimensions, measured at the table top, were equal to X=65 cm and Y=63 cm. All measurements were performed in the solid water phantom under conditions identical to the conditions of the treatment (i.e., with the same distance from the radiation source to the planar top surface of the table, with attenuator filters placed in the beam unless specified otherwise, etc.). The phantom used had lateral dimensions of 30 cm×30 cm and was enclosed inside the bolus of rice bags that provided full scattering from the radiation field.

EXAMPLES 1–3 AND COMPARISON EXAMPLES A–C

In Examples 1–3, film penumbra measurements were made for a moving block (i.e., a block which moves with respect to the table during the table's motion). In Comparison Examples A–C, film penumbra measurements were made for a stationary block (i.e., a block not moving with respect to the table during the table's motion).

The film penumbrae for the moving and stationary blocks in Examples 1–3 and Comparison Examples A–C were measured using 26-centimeter thick solid water phantoms under standard conditions of treatment.

In each example, the block was disposed five (5) centimeters above the phantom surface, and the speed of the table was set so as to deliver 120 cGy to the midplane of the phantom.

In Example 1 and Comparison Example A, a verification film was disposed three (3) centimeters below the anterior surface of the phantom. In Example 2 and Comparison Example B, a verification film was disposed at the midplane of the phantom. In Example 3 and Comparison Example C, a verification film was disposed three (3) centimeters above the posterior surface of the phantom. Thus, with depth being measured from the anterior surface of the phantom, the depth of the film in Example 1 and Comparison Example A was 3 cm, the depth of the film in Example 2 and Comparison Example 2 was 13 cm, and the depth of the film tray in Example 3 and Comparison Example C was 23 cm.

The film penumbrae obtained in Examples 1–3 and Comparison Examples A–C are set forth in Table I. In Table I, the film penumbrae are recorded as the difference in centimeters between the 80% and 20% optical density.

TABLE I

Examples 1–3 and Comparison Examples A–C
Penumbra Comparison: Stationary vs. Moving Blocks

| Example No. | Depth (cm) | Penumbra (cm) |
|---|---|---|
| 1 | 3 | 2.0 |
| A | 3 | 2.4 |
| 2 | 13 | 0.5 |
| B | 13 | 4.4 |
| 3 | 23 | 3.0 |
| C | 23 | >6.5 |

EXAMPLES 4–13 AND COMPARISON EXAMPLE D

To obtain comprehensive information about dose distribution during actual patient irradiation, film and TLD dose measurements in human Rando phantom were performed in Examples 4–13 and Comparison Example D.

Shielding blocks were prepared for the Rando phantom so as to allow proper screening of the lung during the time of the Rando phantom treatment. The shielding blocks were 1.8 cm thick Cerrobend alloy blocks. The shape of the blocks was determined using localization film at the table position routinely used as a reference, where the lungs are approximately centered in the non-moving field. The blocks were drawn on the film in the conventional manner and straight-edge blocks were cut from the films.

Measurements of the Rando phantom's thickness at umbilicus and elevation at umbilicus over the table surface were made. Verification film was cut to correspond to a given slice and sandwiched between slices of the Rando phantom. The film slices secured in the phantom were sealed with electrical tape to prevent light leaks.

The Rando phantom was then placed on the moving table apparatus in supine (and later prone) position and bolused in the exact manner as is a patient undergoing treatment. The dose (160 cGy) was prescribed to the midplane of the Rando phantom at the umbilicus level.

The Rando phantom treatment was performed in the same manner as is a patient treatment with one-half of the dose being delivered AP and the other half PA.

At the time of exposure, the table was moving with a speed determined for D=160 cGy. To achieve the accurate shielding of the lung, the block tray was moved during the time of exposure with respect to the table with a velocity $V_2$. Moreover, the verification film disposed on the film tray during the time of exposure was moved relative to the table with a velocity $V_3$.

Several calibration films were exposed in the range of 30–200 cGy, 10×10 cm2 field, 80 cm SAD using stationary Cobalt 60 teletherapy. All films, calibration and from Rando, were processed at the same time to eliminate errors in readings due to processing variations. Densitometer scans were performed and isodose curves were taken. The results of the film measurements are presented in Table II hereinbelow.

At the time the film dosimetry measurements were being made in the Rando phantom, TLD measurements were also conducted. LiF chips having dimensions of 3 mm×3 mm×0.8 mm were placed in the Rando phantom slices to verify the accuracy of the formulas for table speed. Table speed $V_1$ was calculated so that the right cumulative dose to the body is delivered. Thus, TLD readings were used to verify the accuracy of the speed calculations. The TLD readings were also used to check the correlation between fluorescent dosimetry and the film dose readings. Thus, the TLD chips were located in as close vicinity of the sliced verification films in the Rando phantom as possible. Symmetry was used whenever possible, resulting in two readings for a given depth, off-axis distance, and longitudinal coordinate. The TLD chips were irradiated in the Rando phantom together with the film slices. Results of the TLD measurements are also presented in Table II.

TABLE II

Examples 4–13 and Comparison Example D
TLD and Film Isodose Comparison

| Example No. | Anatomy | Film Isodose (%) | TLD (%) |
|---|---|---|---|
| 4 | Head (midplane) | 95–100 | 96.4 |
| 5 | Neck (midplane) | 105–110 | 102.4 |
| 6 | Lung (shielded, anterior) | 60 | 59.1 |
| 7 | Lung (shielded, midplane) | 60–65 | 64.4 |
| 8 | Lung (shielded, posterior) | 55–60 | 53.8 |

TABLE II-continued

Examples 4–13 and Comparison Example D
TLD and Film Isodose Comparison

| Example No. | Anatomy | Film Isodose (%) | TLD (%) |
| --- | --- | --- | --- |
| 9 | Abdomen (anterior) | 95–100 | 98.1 |
| 10 | Abdomen (midplane) | 102–105 | 104.4 |
| 11 | Abdomen (posterior) | 105–107 | 107.5 |
| 12 | Lower Abdomen (midplane) | 100–105 | 95.6 |
| 13 | Pelvis (posterior) | 98 | 101.9 |
| D | Lung (Unshielded) | 95–100 | 98.75 |

The results presented in Table II show that an effective lung blocking of approximately 55–60% was achieved with the 1.8 cm cerrobend blocks as planned.

Thus, as pointed out previously herein, the advantages of the movable table apparatus and moving-table TBI method of the present invention, wherein dynamic shielding and, preferably, dynamic film verification are provided, may be summarized as follows:

(1) the apparatus and method provide superior dose distribution uniformity throughout the patient's body;

(2) the apparatus and method provide precise shielding of sensitive organs during the TBI therapy;

(3) the apparatus and method allow accurate verification of such shielding of sensitive organs;

(4) the apparatus and method allow the patient to be disposed in a relatively comfortable supine or prone position on the planar top surface of the table; and (5) the apparatus and method are relatively economical and allow relatively easy standardization of setups, calculations and verifications.

What is claimed is:

1. A dynamic table/shield apparatus for effecting total body irradiation treatment of a body while shielding a midplane of a predetermined part of said body from a radiation beam emitted from a radiation source used in said treatment, said apparatus comprising:

(A) a movable treatment table having movement in a first direction at a first velocity, said table comprising a top planar portion for repose thereon of said body; and (B) at least one movable radiation-shielding block for shielding said midplane of said predetermined body part, said block having movement relative to said table in a second direction opposite of said first direction and at a second velocity relative to said table, said second velocity being calculated according to the formula $V_2=(V_1)(b/a)$, wherein "$V_2$" is the second velocity, "$V_1$" is the first velocity, "b" is the perpendicular distance between the shielding block and the midplane of said predetermined body part, and "a" is the perpendicular distance between the radiation source and the midplane of said predetermined body part.

2. An apparatus according to claim 1, wherein said first direction is a horizontal direction extending along a longitudinal axis of said table.

3. An apparatus according to claim 1, wherein said table and said shielding block each have linear movement in said first direction.

4. An apparatus according to claim 1, further comprising a verification film component, wherein the verification film component is disposed at a distance under said top portion of said table, said verification film component having movement relative to said table in said first direction and at a third velocity relative to said table, said third velocity being calculated according to the formula $V_3=(V_1)(b'/a)$ wherein "$V_3$" is the third velocity, "$V_1$" is the first velocity. "b'" is the perpendicular distance between the verification film component and the midplane of said predetermined body part, and "a" is the perpendicular distance between the radiation source and the midplane of said predetermined body part.

5. An apparatus according to claim 4, wherein said first direction is a horizontal direction extending along a longitudinal axis of said table.

6. An apparatus according to claim 4, wherein said film component has linear movement in said first direction.

7. An apparatus according to claim 1, further comprising a first motor for effecting said movement of the treatment table and a second motor for effecting said movement of the shielding block relative to said table.

8. An apparatus according to claim 4, further comprising a first motor for effecting said movement of the treatment table, a second motor for effecting said movement of the shielding block relative to said table, and a gear mechanism for effecting said movement of said verification film component.

9. A method of effecting total body irradiation treatment of a body while shielding a midplane of a predetermined part of said body from a radiation beam emitted from a radiation source used in said treatment, said method comprising:

(1) a dynamic table/shield apparatus comprising:

(A) a movable treatment table having movement in a first direction at a first velocity, said table comprising a top planar portion for repose thereon of said body; and (B) at least one movable radiation-shielding block for shielding said midplane of said predetermined body part, said block having movement relative to said table in a second direction opposite of said first direction and at a second velocity relative to said table, said second velocity being calculated according to the formula $V_2=(V_1)(b/a)$, wherein "$V_2$" is the second velocity, "$V_1$" is the first velocity, "b" is the perpendicular distance between the shielding block and the midplane of said predetermined body part, and "a" is the perpendicular distance between the radiation source and the midplane of said predetermined body part;

(2) providing said radiation source and causing said radiation source to emit said radiation beam toward a plane of said table such that a central axis of said beam is perpendicular to said plane, said beam forming a radiation field on said plane;

(3) placing said body on said treatment table such that a front end of said midplane of said predetermined body part is disposed toward said radiation field and an opposite back end of said midplane of said body part is disposed away from said radiation field;

(4) causing said table to move at said first velocity in said first direction through said radiation field such that said front end of said midplane of said body part enters said radiation field before said back end of said midplane of said body part;

(5) before or during step (4), aligning said shielding block and said midplane of said predetermined body part such that when said midplane is disposed in a beam-entry position, said shielding block is disposed in an initial block position; wherein in said beam-entry position, said midplane is disposed such that a first diverging edge of said beam is aligned so as to contact a front end of said midplane of said body part; further wherein in said initial block position, said shielding block is disposed such that a front end of said block is in contact with said first diverging edge of said beam so as to shield said midplane of said body part from said first diverging edge; and (6) when said shielding block is disposed in said initial block position and said midplane of said body part is disposed in said beam-entry position, causing said shielding block to move in said second direction relative to said table at said second velocity relative to said table; whereby during movement of said table through said radiation field, said midplane of said predetermined body part is continuously and completely shielded from said radiation beam by said shielding block.

10. A method according to claim 9, wherein said first direction is a horizontal direction extending along a longitudinal axis of said table.

11. A method according to claim 9, wherein said table and said shielding block each move in linear fashion.

12. A method according to claim 9, wherein said apparatus further comprises a verification film component disposed at a distance under said top portion of said table, said verification film component having movement relative to said table in said first direction at a third velocity relative to said table, said third velocity being calculated according to the formula $V_3=(V_1)(b'/a)$ wherein "$V_3$" is the third velocity, "$V_1$" is the first velocity, "b'" is the perpendicular distance between the verification film component and the midplane of said predetermined body part, and "a" is the perpendicular distance between the radiation source and the midplane of said predetermined body part; wherein said method further comprises:

(7) aligning said verification film component with said table and said shielding block such that when said midplane of said body part is disposed in said beam-entry position and said shielding block is disposed in said initial block position, said verification film component is disposed in an initial film position, wherein in said initial film position, said film component is disposed such that a point on a front end of said film component forms a straight line with a point disposed on said front end of said shielding block and a point disposed on said first diverging end of said beam; and (8) when said shielding block is disposed in said initial block position, said midplane of said body part is disposed in said beam-entry position, and said film component is disposed in said initial film position, causing said film component to move in said first direction at said third velocity, whereby during passage of said table through said radiation field, images of said shielding block and said midplane of said predetermined body part are formed on said film component.

13. A method according to claim 9, wherein said predetermined body part is an internal organ.

14. A method according to claim 9, wherein said predetermined body part comprises one or both lungs.

15. A method according to claim 9, wherein said patient is disposed on said treatment table in a supine or prone position.

* * * * *